(12) United States Patent
Nguyen

(10) Patent No.: US 6,450,168 B1
(45) Date of Patent: Sep. 17, 2002

(54) INFANT SLEEPING BLANKET/GARMENT FOR USE WITH MEDICAL DEVICES

(75) Inventor: Kellie I. Nguyen, 338 S. 900 East, Orem, UT (US) 84097

(73) Assignee: Kellie I. Nguyen, Odgen, UT (US)

(*) Notice: Subject to any disclaimer, the term of this patent is extended or adjusted under 35 U.S.C. 154(b) by 0 days.

(21) Appl. No.: 09/835,394

(22) Filed: Apr. 17, 2001

(51) Int. Cl.[7] ............................................. A61B 19/00
(52) U.S. Cl. ...................... 128/869; 128/872; 128/877
(58) Field of Search .............................. 128/869, 872, 128/873, 874, 875, 877; 2/69, 102, 114

(56) References Cited

U.S. PATENT DOCUMENTS

| 1,556,747 A | * | 10/1925 | Bates |  |
|---|---|---|---|---|
| 4,206,512 A | * | 6/1980 | Osborne | 2/69.5 |
| 4,688,270 A | * | 8/1987 | Denicola | 128/874 |
| 4,895,162 A |  | 1/1990 | Dolliver |  |
| 5,241,300 A |  | 8/1993 | Buschman |  |
| 5,293,840 A | * | 3/1994 | Wedlick | 128/874 |
| 5,454,376 A |  | 10/1995 | Stephens et al. |  |
| 5,727,562 A |  | 3/1998 | Beck |  |
| 5,852,005 A |  | 12/1998 | Scanlon |  |
| 5,928,157 A |  | 7/1999 | O'Dwyer |  |
| 6,047,201 A |  | 4/2000 | Jackson, III |  |

* cited by examiner

Primary Examiner—Michael A. Brown

(57) ABSTRACT

An infant's sleep blanket/garment for use with medical monitoring devices, which is offered as either a sleep sack or a sleep shirt, depending on the age of the infant, with the sleep sack further presented with no arm holes and having snugging straps for newborns or with arm holes and sleeves for older infants. An openable monitor cable sheath located inside of the sleeper allows for bundling medical monitoring device cables and IV tubes and enclosing them within the sheath to prevent irritation to the infant and reduce the possibility of the infant becoming entangled in the cables and tubes. Additionally, the upper shoulder and sleeve seams are openable to allow for the installation, maintenance and removal of IV tubes without removing the garment from the infant. Thermometers incorporated into the body of the garment and an optional sleep cap aid in monitoring the infant's temperature as he sleeps.

18 Claims, 6 Drawing Sheets

INFANT SLEEPING BLANKET/GARMENT FOR USE WITH MEDICAL DEVICES

BACKGROUND OF THE INVENTION

1. Field of the Invention

The present invention relates to the monitoring of vital signs of infants. More particularly, the invention comprises a sleeping blanket/garment and cap set incorporating provisions for use with monitoring devices to warn of the onset of incidents such as Sudden Infant Death Syndrome (SIDS), apnea or other respiratory or heart emergencies.

2. Description of the Prior Art

SIDS is the main cause of death among infants between one week and twelve months of age. Overheating and re-breathing carbon dioxide, which can get trapped in blankets and loose objects, are highly suspected links to SIDS. A number of methods of monitoring infants have been propounded over the years, using various methods of attachment of transducers to the monitored infant, with varying degrees of success.

U.S. Pat. No. 6,047,201, issued to William H. Jackson, III, on Apr. 4, 2000, presents an INFANT BLOOD OXYGEN MONITOR AND SIDS WARNING DEVICE, a device to monitor blood oxygen levels and pulse rate of an infant. A foot and ankle wrap containing a rechargeable battery and radio transmitter is connected to a toe cap containing a pulse oximeter. Blood oxygen level and pulse are transmitted to a receiver which sounds an alarm if the blood oxygen drops to a predetermined level for a predetermined period of time.

U.S. Pat. No. 5,928,157, issued to Joseph E. O'Dwyer on Jul. 27, 1999, presents an APNEA DETECTION MONITOR WITH REMOTE RECEIVER, wherein a strap having motion sensors and a transmitter is fitted around an infant's chest. Physical motion is converted to electronic signals which are processed by a comparator. As long as the infant is breathing within predetermined parameters the motion will be accepted as normal. If breathing becomes abnormal or ceases, the comparator will consider the movement as abnormal and the transmitter will transmit an alert signal to a remote receiver.

U.S. Pat. No. 5,853,005, issued to Michael V. Scanlon on Dec. 29, 1998, presents an ACOUSTIC MONITORING SYSTEM, in which a transducer in communication with fluid in a pad receives acoustic signals, such as heart beat or breathing, transferred to the fluid by a body in close contact with the pad. The acoustic signals may be processed at the site of the monitoring system or transmitted to a remote receiver to sound an alarm if the acoustic signal changes or is interrupted, as changes in pulse or breathing rhythm, as might be caused by SIDS or apnea.

U.S. Pat. No. 5,727,562, issued to Gregory S. Beck on Mar. 17, 1998, presents a PNEUMATICALLY SENSED RESPIRATION MONITOR & METHOD, in which a flexible, gas filled belt is fitted around the chest of an infant to monitor respiration. As the infant inhales, pressure within the belt increases due to the expansion of the chest, opening a pressure switch. Conversely, as the infant exhales, pressure within the belt decreases, closing the pressure switch. Should the respiration interval exceed a predetermined period of time, a timing circuit sounds an audible alarm, warning an attendant of the change in respiration interval.

U.S. Pat. No. 5,454,376, issued to David L. Stephens, et. al., on Oct. 3, 1995, presents BREATHING MONITOR ARTICLES OF WEARING APPAREL, teaches a garment for an infant in which a shirt or similar garment contains a pocket having a monitor therein. An elastic band or bands extend around the garment in the region of the chest and/or abdomen, each band having a strain gauge secured thereto. The electronic monitor generates an alarm signal if there is a cessation of breathing for a predetermined period of time.

U.S. Pat. No. 5,241,300, issued to Johannes Buschmann on Aug. 31, 1993, presents a SIDS DETECTION APPARATUS AND METHODS, teaches a garment which is fabricated with a series of transilluminated optical fibers encircling an infants chest and/or abdomen. Movement of the fibers causes a modulation of the intensity of the light transmitted to a monitor, therefore, cessation of movement for a predetermined period of time can be detected and an alarm sounded.

U.S. Pat. No. 4,895,162, issued to Maria Dolliver on Jan. 23, 1990, presents an APNEA MONITOR BELT, in which a soft belt containing a pair of electrodes is positioned around the torso of an infant such that the electrodes are in position to monitor vital signs, such as respiration and pulse. Monitoring lead wires connect the electrodes to a monitor unit proximate the infant.

In contrast to each of the above, the present invention is intended to serve as a vehicle for facilitating the use of various independent medical devices without the danger of an infant becoming entangled in tubes or cords by channeling such tubes and cords through an internal sheath, while an openable shoulder seam allows for installation, maintenance and removal of medical devices along the arm and shoulder without having to remove the garment.

None of the above inventions and patents, taken either singly or in combination, is seen to describe the instant invention as claimed.

SUMMARY OF THE INVENTION

The present invention features a sleeping blanket/garment which provides for snug sleeping comfort for an infant while providing easy access for medical devices, such as respiration or cardiac monitors, intravenous (IV) tubes, and the like, as might be used for monitoring for conditions such as overheating, which can lead to SIDS or apnea. The garment can be made as either a sleeper sack, totally enclosing the infant below the neck, to a sleeved, sleeper sack or shirt for older infants. Both the sleeper blanket/garment and a sleep cap have provisions for a flat thermometer incorporated into their design for ease in monitoring the infants temperature without having to remove the blanket/garment for temperature taking.

Accordingly, it is a principal object of the invention to provide a sleeping blanket/garment which provides channels to direct lines such as monitor cables and IV tubes through specific channels in order to prevent tangling or crimping.

It is a further object of the invention to provide a sleeping blanket/garment and cap which facilitate the monitoring of the infants temperature to prevent overheating, which is a suspected link to SIDS.

It is another object of the invention to provide a sleeping blanket/garment which can easily be made as either a full sleeper sack for newborns to a sleeved sleeper sack or shirt for older infants.

Still another object of the invention is to provide a sleeping blanket/garment which provides snug sleeping comfort for an infant, as an infant is calmed when bundled snugly to resemble its snug position while in utero.

Another object of the invention is to provide a sleeping blanket/garment which will facilitate the warmth of the infant so that blankets, which have been deemed hazardous because of the risk of trapping a baby's exhaled carbon dioxide and causing asphyxiation leading to SIDS, can be eliminated from use while also allowing the use of attached monitoring equipment simultaneously.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
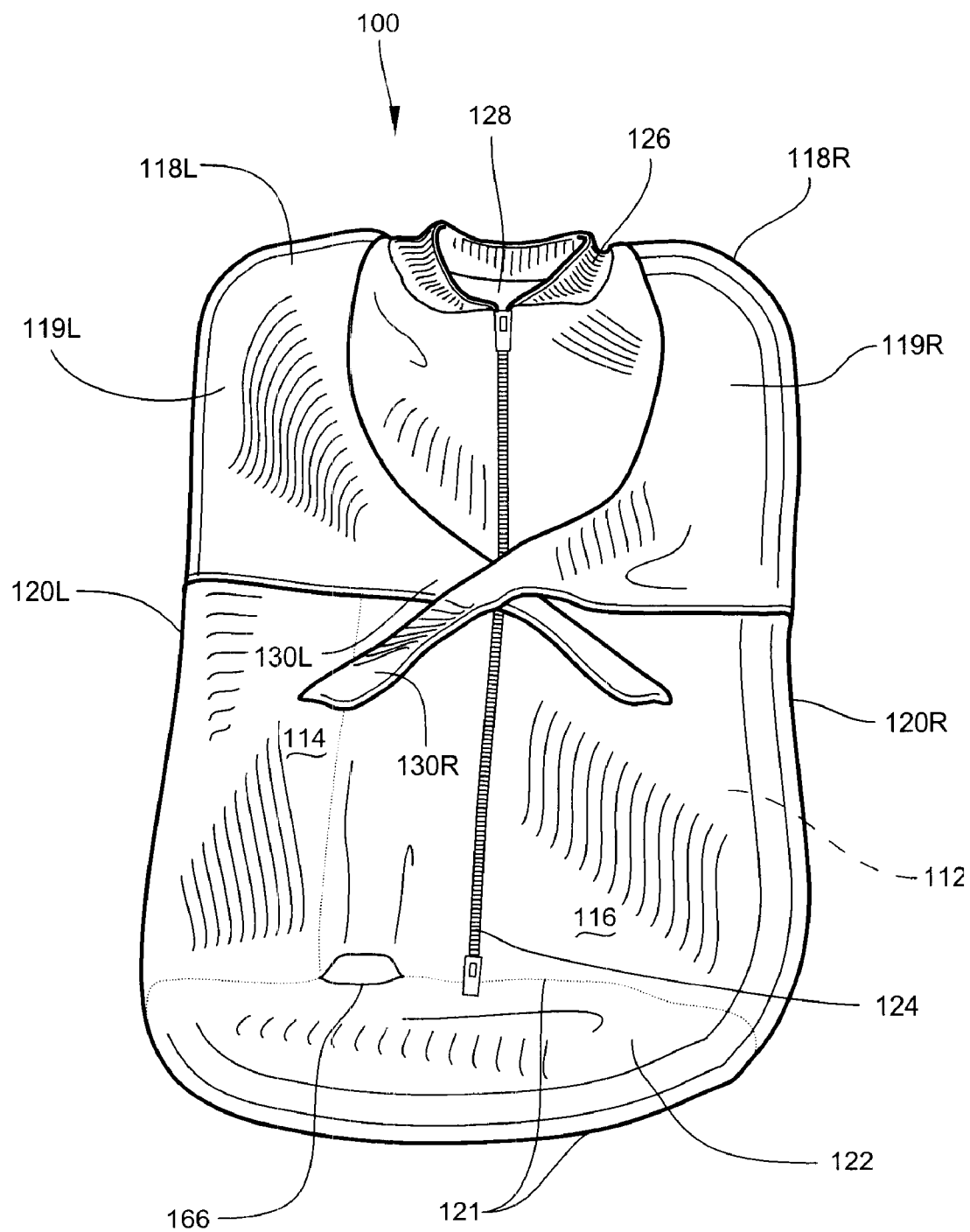
FIG. 1 is a front perspective view of a armless sleep sack of the invention.
Figure 2:
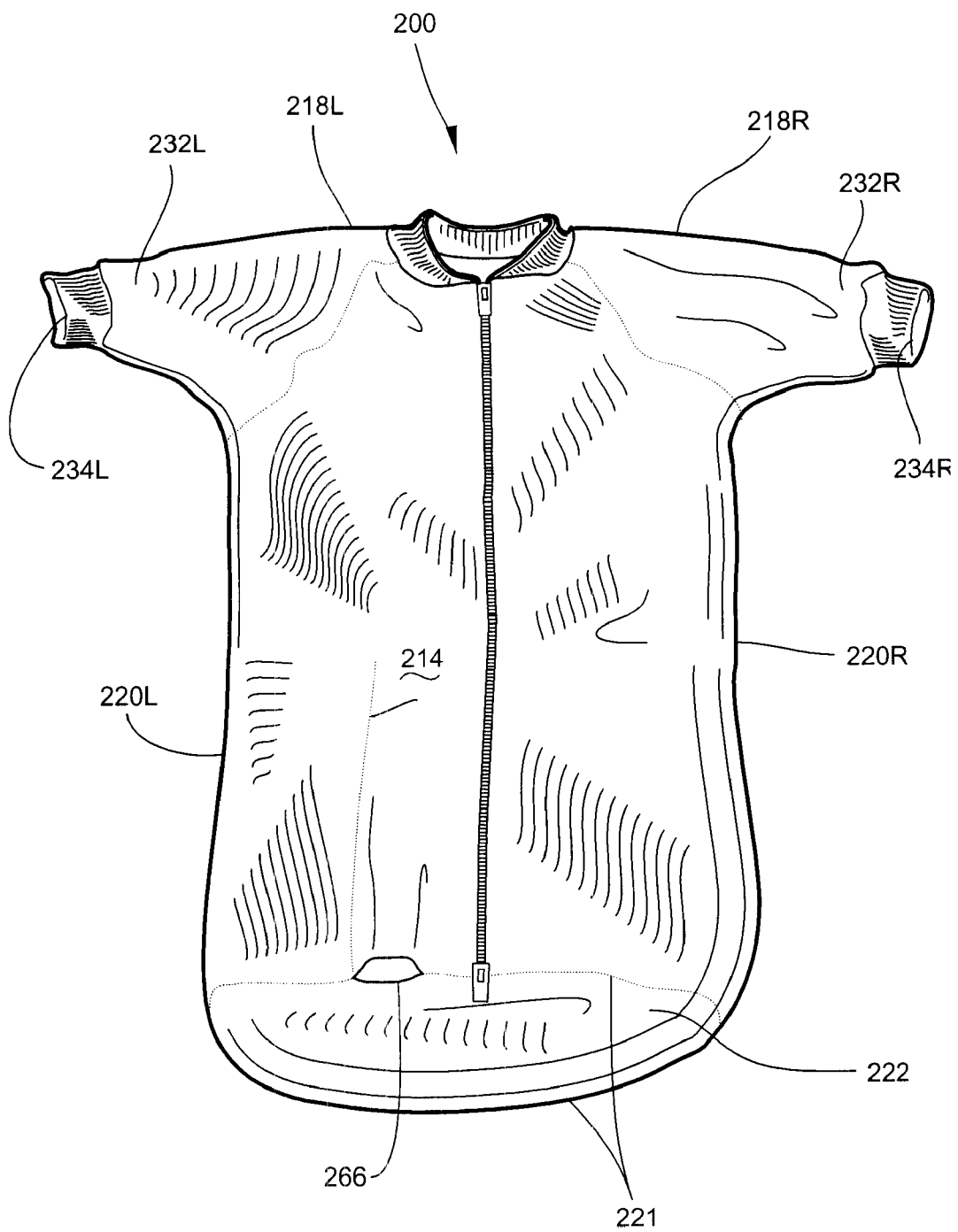
FIG. 2 is a front perspective view of a sleeved sleep sack of the invention.
Figure 3:
FIG. 3 is front perspective view of a sleep shirt of the invention.

The sleeping blanket/garment of the present invention is intended to be produced in sizes ranging from premature infant to toddler, and as either a sleep sack or sleep shirt. The sleep sack may be produced in either a sleeved or sleeveless (i.e., having no arm holes) version. For the sake of illustration, FIG. 1 presents the sleeveless version of the sleep sack, FIG. 2 presents the sleeved version of the sleep sack, and FIG. 3 presents the sleep shirt. Various additional elements can be applied to any of the embodiments, although typically they will be illustrated in only one Figure. Like reference numbers will be used in each throughout, with the exception that the first digit will correspond to the FIG. number.

Referring now to FIG. 1, sleep sack 100 has a back panel, 112 which is attached to a left front panel 114 and a right front panel 116 by sewn seams 118L and 118R along the respective shoulders 119L and 119R, down the respective side seams 120L and 120R, and seam 121 around the bottom 122 of sleep sack 100. A two way zipper 124 which opens from either the top or the bottom, or other closure, such as, but not limited to snaps, buttons or Velcro®, closes the juncture between left front panel 114 and right front left panel 116. A collar band 126 surrounds a neck opening 128 at the upper end of two way zipper 124 between shoulders 118L and 118R. Snugging straps 130L and 130R are sewn into the seams 118L and 118R of shoulders 119L and 119R and the upper portion of side seams 120L and 120R for securing sleep sack 100 more snugly around an infant (not shown).

Referring now to FIG. 2, the construction of basic sleep sack 200 is identical to that of sleep sack 100, FIG. 1, with the exception that sleeves 232L and 232R are sewn at the seams 218L and 218R of shoulders 219L and 219R and the upper portions of side seams 220L and 220R. Sleeves 232L and 232R terminate in cuff bands 234L and 234R, respectively.

Referring now to FIG. 3, construction of sleep shirt 300 is, again, basically identical to that of sleep sack 200, FIG. 2, with the exception that the bottom region 322 of sleep shirt 300 is open. It would be evident to one skilled in the art, however, that bottom 322 could have a closure element 336 such as, but not limited to a zipper, snaps, buttons or Velcro® to, in effect, convert sleep shirt 300 to a sleep sack.

Figure 4:
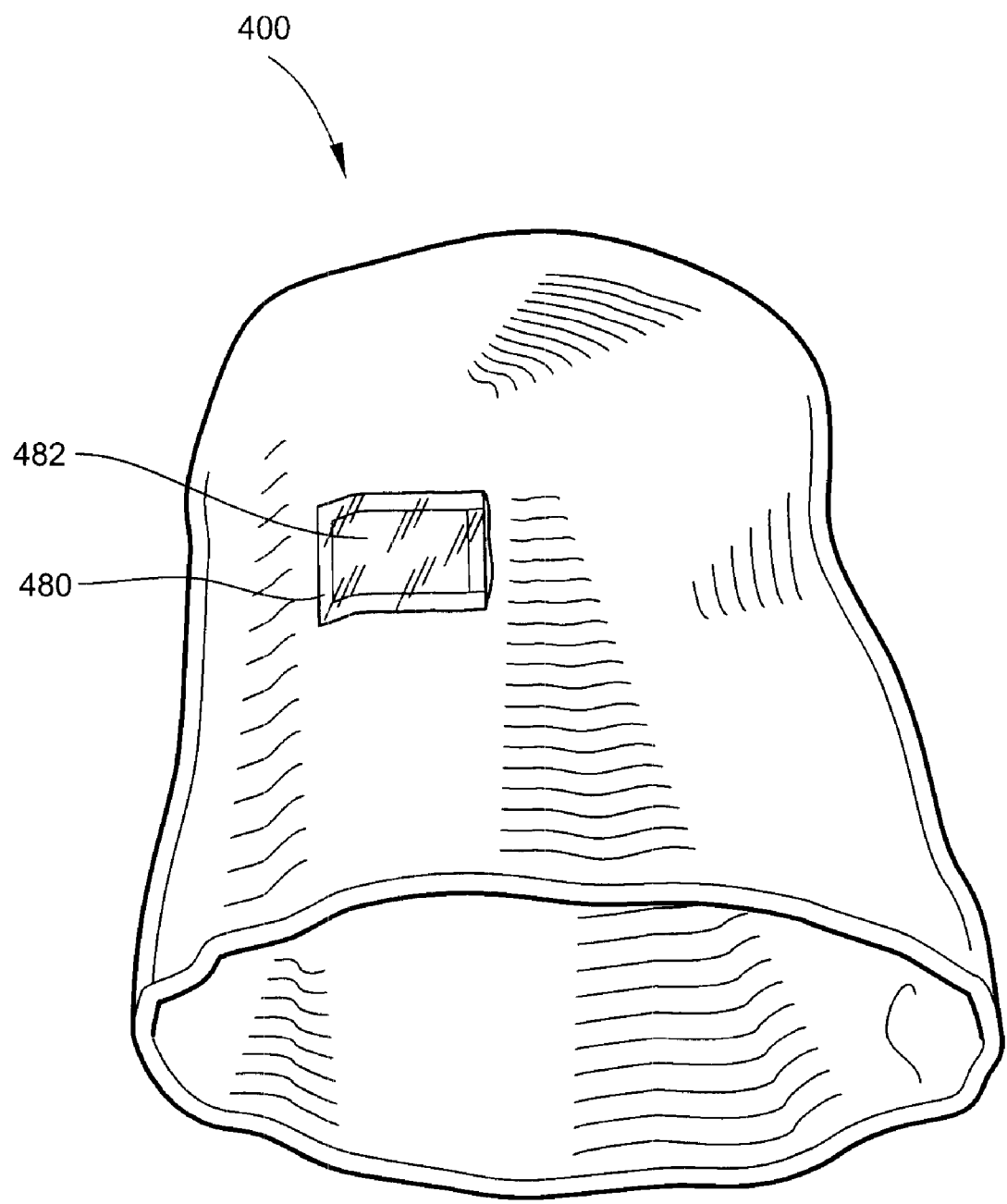
FIG. 4 is a front perspective view of the sleep cap of the invention.

Referring now to FIG. 4, a cap 400 aids in keeping the infants head warm and may include a monitoring device, which will be discussed later.

It would be evident to one skilled in the art that sleeper sacks 100 and 200, sleeper shirt 300 and cap 400 could be made of a variety of different materials, so long as they provide warm, soft, non-irritating and non-flammable comfort to the wearer. Likewise, while comfort is important, the exact styles of sleeper sacks 100 and 200, sleeper shirt 300 and cap 400 are not of great importance to the overall invention, as they are primarily vehicles for the following additional elements of the invention. Designs presented in FIGS. 1–3 are intended only to be representational.

Figure 5:
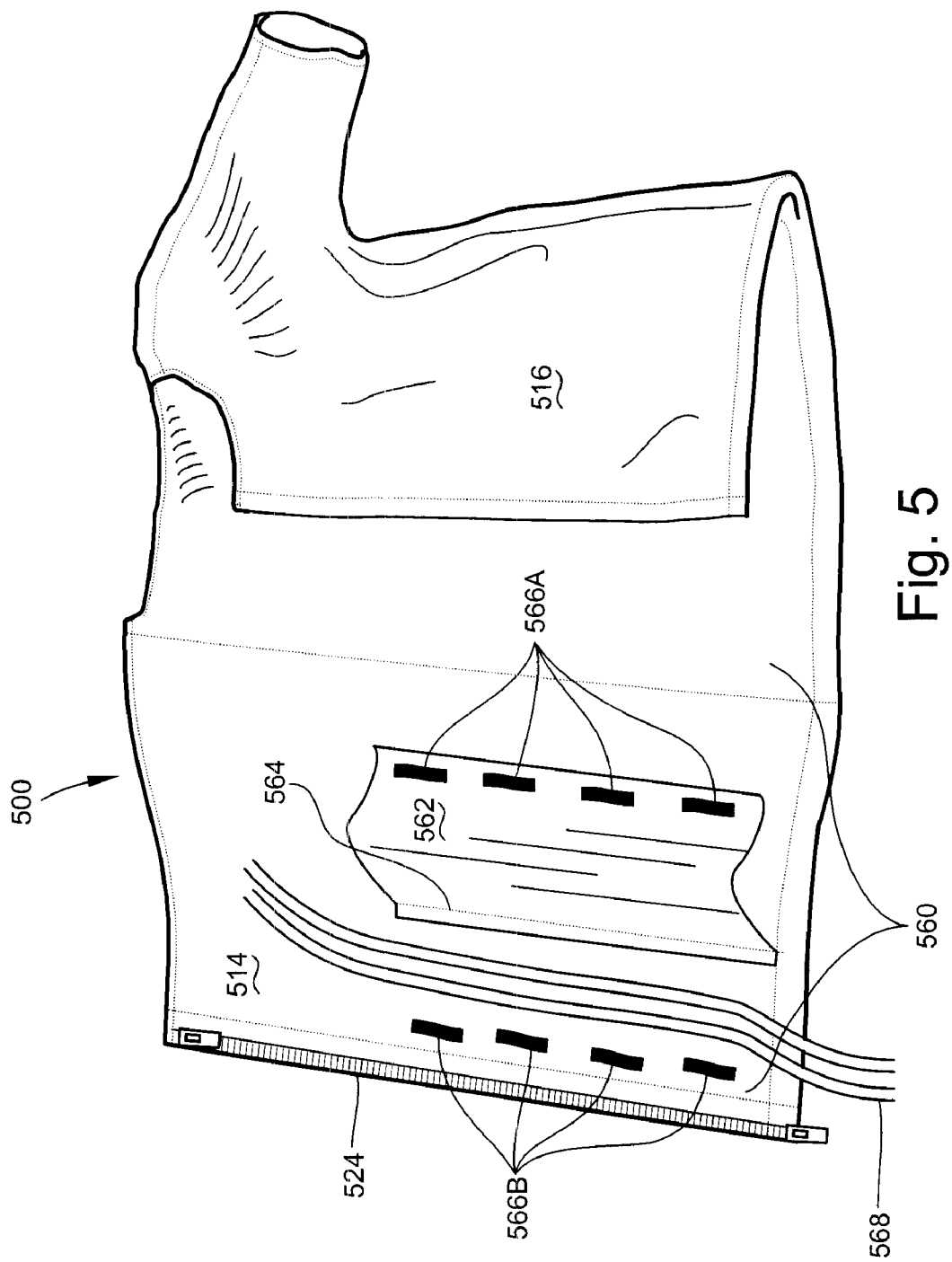
FIG. 5 is a front perspective view of one embodiment of the invention illustrating the monitor sheath.
Figure 6:
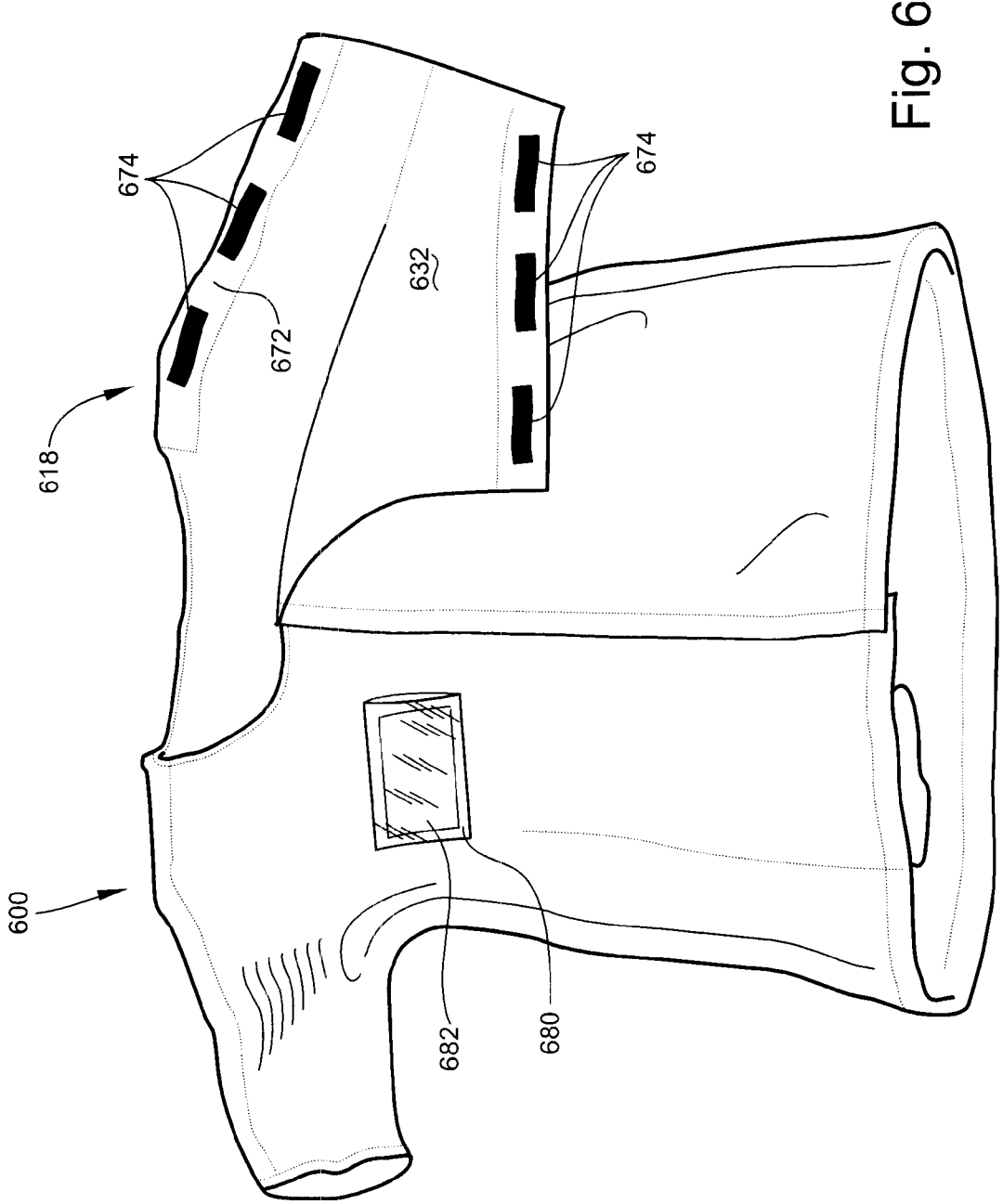
FIG. 6 is a front perspective view of one embodiment of the invention illustrating the openable sleeve and thermometer.

Referring now to FIG. 5 and 6, the following additional elements of the invention are disclosed:

An openable monitor sheath 560 is formed by sewing or otherwise securing a first length edge of monitor cable sheath flap 562, by means of a seam 564 to the inside surface of left front panel 514, typically substantially parallel to and spaced from two way zipper 524. The second length edge of monitor cable sheath flap 562 is equipped with Velcro® fasteners 566a or another suitable closure device is adapted to mate with suitable fasteners 566b positioned along the edge of the inside surface of left front panel 514, proximate two way zipper 524. In the sleep sack version of FIGS. 1 and 2, an opening 166/266 is left in the seam 121/221 between left front panel 114/214 and bottom 120/220 to allow monitor cables to be passed through sleeper sack 100/200. Monitor cable sheath 560 may be used to consolidate and constrain cables 568 leading to any monitors to which the infant may be attached. It would be obvious to one skilled in the art that a number of different ways of securing monitor cable sheath 560 could be use, but obviously, whatever method is used should protect the cables and present a smooth, soft, non-irritating surface to the infant. It should also be obvious that monitor cable sheath could attached to the right front panel 516, in lieu of left front panel 514, or to both left front panel 514 and right front panel 516, with equal effectiveness.

Referring now to FIG. 6, a means of opening sleeve 632L and/or 632R is created by leaving seam 618L and/or 618R open along the upper edge of sleeve 632L and/or 632R. A folded flap 672 extends the back edge of sleeve 632L and/or 632R to facilitate attaching a fastening device 674, such as, but not limited to, Velcro®, along the two edges of what would have been seam 618 such that the seam may be opened and closed for the installation, maintenance and removal of IV tubes and/or monitor cables without having to remove sleep sack 500 from the infant.

In order to easily monitor an infants temperature while he sleeps, a clear plastic sheath 680 containing a flat thermometer 682 may be incorporated into sleeper 600 in any number of locations, including, but not limited to, the chest, the side and the back. A plastic sleeve 480 and thermometer 482 may also be incorporated into the sleep cap 400.

It is to be understood that the present invention is not limited to the embodiments described above, but encompasses any and all embodiments within the scope of the following claims.

What is claimed is:

1. An infant sleeping blanket/garment for use with medical devices comprising:
    a garment, adapted to enclose at least the upper torso of an infant, said garment having
        a top, said top having:
            an opening adapted to surround the neck of the infant, and
            a shoulder region on each of the two sides of said neck opening, said shoulder region adapted to surround the shoulders of the infant enclosed within said garment,
        a bottom,
        a back, and
        a front, said front comprising:
            partable right and left panels, said right left panels being releasably joinable by
            securing means for securing said right and left panels in a joined position,
    means for providing access to the infant's upper torso region for installing, maintaining and removing medical devices without having to remove said garment, and
    means for directing and constraining tubes and cords of medical devices within the length, top to bottom, of said garment and from said garment; and
    wherein said means for directing and constraining tubes and cords of medical devices within the length of said garment and from said garment comprises:
        an openable monitor cable sheath affixed within at least one of said right and left front panels of said garment, said monitor cable sheath further comprising:
            a monitor cable sheath flap affixed by a first edge inside said at least one of said right and left front panels of said garment, substantially parallel to and spaced from said securing means for releasably joining said right and left front panels of said garment,
            a first fastening device element affixed along a second edge of said monitor cable sheath flap, said second edge being substantially parallel said first edge, and
            a second fastening device element adapted to mate with said first fastener device element affixed inside said at least one of said right and left front panels of said garment proximate said securing means,
        the area between said front panel of said garment, said monitor cable sheath flap, said line of affixing of said monitor cable sheath flap to said front panel of said garment, and said first and said second fastener device elements forming a linear sheath for directing and constraining the tubes and cords of medical devices within the confines of said sheath and from said bottom of said garment.

2. An infant sleeping blanket/garment for use with medical devices, as defined in claim 1, wherein said securing means for said right and left front panels of said garment in a joined position comprises one of the group: a two way zipper having two pull tabs and being openable from the upper end and the lower end, a one way zipper having a single pull tab, snaps, buttons and hook and loop fastener.

3. An infant sleeping blanket/garment for use with medical devices, as defined in claim 2, wherein
    said garment is one from the group:
        a sleep sack, being closed at its said bottom, thereby completely enclosing the infant's torso and legs within said sleep sack, and
        a sleep shirt, being open at its said bottom, thereby allowing the infant's legs to protrude from its said bottom.

4. An infant sleeping blanket/garment for use with medical devices, as defined in claim 3, wherein
    said sleep sack configured in one of the styles from the group:
        having no arm openings, whereby the infant's arms are constrained within said sack, and
        having arm openings and sleeves proximate said shoulder regions, whereby the infant's arms are free to be moved about outside of said sleep sack.

5. An infant sleeping blanket/garment for use with medical devices, as defined in claim 4, wherein said sleep sack having no arm openings further comprises:
    a snugging strap affixed exterior of said sleep sack proximate each of said shoulder regions and continuing downwardly a distance from said shoulder regions, said snugging straps facilitating the securing of said sleep sack more snugly around the infant.

6. An infant sleeping blanket/garment for use with medical devices, as defined in claim 1, wherein said means for providing access to the infant's upper torso region within said arm and shoulder region of said garment comprises:
    a partable seam along the top of at least one of said shoulder regions and the upper edge of said sleeve corresponding to each of said at least one shoulder region, said partable seam running fully from said neck opening to the free end of said sleeve and being securable by a closure device within said partable seam, said closure device comprising one of the group: zipper, snaps, buttons and Velcro®.

7. An infant sleeping blanket/garment for use with medical devices, as defined in claim 1, further comprising at least one thermometer, said at least one thermometer adapted to display the temperature of the infant as the infant sleeps.

8. An infant sleeping blanket/garment for use with medical devices, as defined in claim 1, further comprising a sleep cap adapted to keep the head of the infant warm as the infant sleeps.

9. An infant sleeping blanket/garment for use with medical devices, as defined in claim 8, further comprising a thermometer, said thermometer adapted to display the temperature of the infant as the infant sleeps.

10. An infant sleep blanket/garment for use with medical devices comprising:
   a garment, adapted to enclose at least the upper torso of an infant, said garment having
      a top, said top having:
         an opening adapted to surround the neck of the infant, and
         a shoulder region on each of the two sides of said neck opening, said shoulder region adapted to surround the shoulders of the infant enclosed within said garment,
      a front, said front comprising:
         partable right and left panels, said right and left panels being releasably joined by
         securing means, said securing means comprising one of the group: a two way zipper having two pull tabs and being openable from the upper end and the lower end, a one way zipper having a single pull tab, snaps, buttons and Velcro®, and
      a bottom, said bottom joining said back and said front such that said bottom is closed, thereby completely enclosing the infant's torso, arms and legs within said sleep sack, and
      snugging straps affixed exterior of said sleep sack proximate each of the two shoulder regions and continuing downwardly a distance from said shoulder regions, said snugging straps facilitating the securing of said sleep sack snugly around the infant;
   means for directing and constraining tubes and cords of medical devices within the length of said garment and from the bottom of said garment, said means for directing and constraining comprising:
      an openable monitor cable sheath affixed within at least one of said right and left front panels of said garment, said monitor cable sheath further comprising:
         a monitor cable sheath flap affixed by a first edge inside said at least one of said right and left front panels of said garment, substantially parallel to and spaced from said securing means for releasably joining said right and left front panels of said garment,
         a first fastening device element affixed along a second edge of said monitor cable sheath flap, said second edge being substantially parallel said first edge, and
         a second fastening device element adapted to mate with said first fastener device element affixed inside said at least one of said right and left front panels of said garment proximate said securing means,
         the area between said front panel of said garment, said monitor cable sheath flap, said line of affixing said monitor cable sheath flap to said front panel of said garment, and said first and said second fastener device elements forming a linear sheath for directing and constraining the tubes and cords of medical devices within the confines of said sheath, and
         an opening in the seam joining said bottom and said front and aligned with the bottom of said monitor cable sheath, said opening facilitating passing the tubes and cords of medical devices from within the garment to the exterior of the garment.

11. An infant sleep blanket/garment for use with medical devices, as defined in claim 10, further comprising at least one thermometer, the at least one thermometer adapted to display the temperature of the infant as the infant sleeps.

12. An infant sleep blanket/garment for use with medical devices, as defined in claim 10, further comprising:
   a sleep cap adapted to keep the infant's head warm as the infant sleeps.

13. An infant sleep blanket/garment for use with medical devices, as defined in claim 12, the sleep cap further comprising:
   a thermometer, the thermometer adapted to display the temperature of the infant as the infant sleeps.

14. An infant sleep blanket/garment for use with medical devices comprising:
   a garment, adapted to enclose at least the upper torso of an infant, the garment having
      a top, the top having:
         an opening adapted to surround the neck of the infant, and
         a shoulder region on each of the two sides of the neck opening, the shoulder region adapted to surround the shoulders of the infant enclosed within the garment and having an arm opening and sleeve, whereby the infant's arms are free to be moved about outside of the sleep sack,
      a front, the front comprising:
         partable right and left panels, the right and left panels being releasably joined by
         securing means, the securing means comprising one of the group: a two way zipper having two pull tabs and being openable from the upper end and the lower end, a one way zipper having a single pull tab, snaps, buttons and Velcro®, and
      a bottom,
      means for directing and constraining tubes and cords of medical devices within the length of the garment and from the bottom of the garment, the means for directing and constraining comprising:
         an openable monitor cable sheath affixed within at least one of the right and left front panels of the garment, the monitor cable sheath further comprising:
            a monitor cable sheath flap affixed by a first edge inside the at least one of the right and left front panels of the garment, substantially parallel to and spaced from the securing means for releasably joining the right and left front panels of the garment,
            a first fastening device element affixed along a second edge of the monitor cable sheath flap, the second edge being substantially parallel the first edge, and
            a second fastening device element adapted to mate with the first fastener device affixed inside the at least one of the right and left front panels of the garment proximate the securing means,
            the area between the front panel of the garment, the monitor cable sheath flap, the line of affixing the monitor cable sheath flap to the front panel of the garment, and the first and the second fastener device elements forming a linear sheath for directing and constraining the tubes and cords of medical devices within the confines of the sheath.

15. An infant sleep blanket/garment for use with medical devices, as defined in claim 14, wherein the bottom comprises one of the group:
- a bottom panel affixed to the bottom edge of the back and the bottom edges of the right and left front panels, whereby the infant's torso and legs are enclosed within the garment, the bottom having
  - an opening in the seam aligned with the bottom of the monitor cable sheath, the opening facilitating passing the tubes and cords of medical devices from within the garment to the exterior of the garment, and
- a void between the bottom edge of the back and the bottom edges of the right and left front panels, thereby allowing the infant's legs to protrude through the bottom.

16. An infant sleep blanket/garment for use with medical devices, as defined in claim 14, further comprising:
- at least one thermometer, the at least one thermometer adapted to display the temperature of the infant as the infant sleeps.

17. An infant sleep blanket/garment for use with medical devices, as defined in claim 14, further comprising:
- a sleep cap adapted to keep the infant's head warm as the infant sleeps.

18. An infant sleep blanket/garment for use with medical devices, as defined in claim 17, the sleep cap further comprising:
- a thermometer, the said thermometer adapted to display the temperature of the infant as the infant sleeps.

* * * * *